(12) United States Patent
Rice et al.

(10) Patent No.: US 6,376,669 B1
(45) Date of Patent: Apr. 23, 2002

(54) DYE LABELED IMIDAZOQUINOLINE COMPOUNDS

(75) Inventors: Michael J. Rice, Oakdale; Mark A. Tomai; Ai-Ping Wei, both of Woodbury, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/705,072

(22) Filed: Nov. 2, 2000

Related U.S. Application Data

(60) Provisional application No. 60/163,724, filed on Nov. 5, 1999.

(51) Int. Cl.[7] .................. C07D 471/04; C09B 11/08
(52) U.S. Cl. ..................... 546/82; 546/13; 546/118; 544/229; 548/110; 548/405; 549/224; 549/225; 549/226; 549/227
(58) Field of Search ..................... 546/82, 118, 13; 544/229; 548/110, 405; 549/224, 225, 226, 227

(56) References Cited

U.S. PATENT DOCUMENTS

| | | |
|---|---|---|
| 3,314,941 A | 4/1967 | Littell et al. |
| 3,917,624 A | 11/1975 | El-Haj et al. |
| 4,689,338 A | 8/1987 | Gerster |
| 4,698,348 A | 10/1987 | Gerster |
| 4,774,339 A | 9/1988 | Haugland et al. |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,248,782 A | 9/1993 | Haugland et al. |
| 5,266,575 A | 11/1993 | Gerster |
| 5,268,376 A | 12/1993 | Gerster |
| 5,274,113 A | 12/1993 | Kang et al. |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,585,612 A | 12/1996 | Harp, Jr. |
| 5,605,899 A | 2/1997 | Gerster et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,741,909 A | 4/1998 | Gerster et al. |
| 5,886,006 A | 3/1999 | Nikolaides et al. |
| 5,977,366 A | 11/1999 | Gerster et al. |
| 6,069,149 A | 5/2000 | Nanba et al. |

FOREIGN PATENT DOCUMENTS

| | | |
|---|---|---|
| EP | 0 894 797 A1 | 2/1998 |
| JP | 9-208584 | 8/1997 |
| WO | WO 93/09119 | 5/1993 |
| WO | WO 97/48704 | 12/1997 |
| WO | WO 99/29693 | 6/1999 |
| WO | WO 00/06577 | 2/2000 |
| WO | WO 00/09506 | 2/2000 |

OTHER PUBLICATIONS

Wozniak, et al, "The Amination of 3–nitro–1, 5–naphthyridines by Liquid Ammonia/Potassium Permanganate[1,2]. A New and Convenient Amination Method.", *Journal of the Royal Netherlands Chemical Society*, 102, pp 511–513, Dec. 12, 1983.

Brennan, et al, "Automated Bioassay of Interferons in Micro–test Plates", *Biotechniques*, Jun./Jul., 78, 1983.

Testerman, et al, "Cytokine Induction by the Immunomodulators Imiquimod and S–27609", *Journal of Leukocyte Biology*, vol. 58, pp. 365–372, Sep. 1995.

Bachman, et al, "Synthesis of Substituted Quinolylamines. Derivatives of 4–Amino–7–Chloroquinoline", *J. Org. Chem.*, 15, pp 1278–1284 (1950).

Jain, et al, "Chemical and Pharmacological Investigations of Some ω–Substituted Alkylamino–3–aminopyridines", *J. Med. Chem.*, 11, pp 87–92 (1968).

Baranov, et al., *Chem. Abs.* 85, 94371, (1976).

Berényi, et al, "Ring Transformation of Condensed Dihydro–as–triazines", *J. Heterocyclic Chem.*, 18, pp 1537–1540 (1981).

Gibson et al. "Cellular Requirements for Cytokine Production in Response to the Immunomodulators Imiquimod and S–27609", *Journal of Interferon and Cytokine Research*, 15, 537–545 (1995).

*Primary Examiner*—Evelyn Mei Huang
(74) *Attorney, Agent, or Firm*—MarySusan Howard; Ted K. Ringsred; Robert W. Sprague (57) ABSTRACT

Dye labeled imidazonaphthyridine, imidazopyridine and imidazoquinoline compounds having immune response modulating activity are disclosed. The compounds are useful, inter alia, for determining the binding and/or receptor sites of the molecules.

11 Claims, 1 Drawing Sheet

DYE LABELED IMIDAZOQUINOLINE COMPOUNDS

This application claims the benefit of provisional application 60/163,724, filed Nov. 5, 1999.

FIELD OF THE INVENTION

The invention relates to imidazonaphthyridine, imidazopyridine and imidazoquinoline compounds that have immune response modulating activity and that contain a dye moiety, in particular, a fluorescent dye moiety. The invention also relates to methods of preparing the dye labeled compounds.

BACKGROUND OF THE INVENTION

Compounds that are labeled or tagged have long been used in the chemical and biological sciences. Such compounds can be used in a variety of ways. For example, by labeling a compound that is known to be biologically active, one can more readily identify metabolites of the compound, one can determine the binding and/or receptor sites for the molecule, one can determine how long the compound remains in the body or other system, and so on.

One known way to label compounds is by attaching a dye marker to the compound. This is typically done by grafting a dye moiety onto the biologically active molecule or by incorporating the dye moiety into the biologically active molecule during its synthesis. It is important that the labeled compound retain the critical properties of the unlabeled compound such as selective binding to a receptor or nucleic acid, activation or inhibition of a particular enzyme, or ability to incorporate into a biological membrane. There are a wide variety of dye moieties available, including for example, dipyrrometheneboron difluoride dyes, fluorescein, fluorescein derivatives, rhodamine, rhodamine derivatives and Texas Red.

The imidazonaphthyridines, imidazopyridines and imidazoquinolines are part of a unique class of immune response modifier compounds that have the ability to induce the biosynthesis of interferon and other cytokines. See, for example, Gerster, U.S. Pat. No. 4,689,338; Gerster et al., U.S. Pat. No. 4,929,624; Gerster, U.S. Pat. No. 5,268,376; Gerster et al., U.S. Pat. No. 5,389,640; Nikolaides et al., U.S. Pat. No. 5,352,784; Lindstrom et al., U.S. Pat. No. 5,494,916; and International Publication WO 99/29693. Dyes, particularly fluorescent dyes, are typically relatively large, bulky molecules and it is possible that such a large substituent may impair the compound's ability to bind or otherwise interact with the subject cells in a manner that causes biologic response.

SUMMARY OF THE INVENTION

We have discovered a class of dye labeled imidazonaphthyridine, imidazopyridine or imidazoquinoline compounds that retain their ability to induce cytokines. These compounds employ a spacer group to separate the dye moiety from the active core of the compound so that the bulky dye group does not interfere with the biological activity of the molecule. The compounds of the invention have the generic formula (I):

wherein:

$R_1$ is a spacer group;

$R_2$ is hydrogen, alkyl, hydroxyalkyl, haloalkyl, aminoalkyl, alkylaminoalkyl, dialkylaminoalkyl, amidoalkyl, alkylamidoalkyl, dialkylamidoalkyl, alkanoylalkyl, azidoalkyl, carbamoylalkyl, alkyl optionally interrupted by a heteroatom; alkenyl, alkenyloxyalkyl; cycloalkylalkyl, heterocycloalkyl; aryl, aralkyl, aralkenyl, heteroarylalkyl, in which aryl is optionally substituted by alkyl of 1 to 4 carbon atoms, alkoxy of 1 to 4 carbon atoms, halo, amino, alkylamino or dialkylamino; aroylalkyl, or heteroaroylalkyl;

$R_3$ and $R_4$ are each independently hydrogen, alkyl, alkoxy of 1 to 4 carbon atoms, halo, amino, alkylamino, dialkylamino, or when taken together, $R_3$ and $R_4$ form a fused aryl or heteroaryl group that is optionally substituted by one or more substituents selected from alkyl of 1 to 4 carbon atoms, alkoxy of 1 to 4 carbon atoms, halo, amino, alkylamino, dialkylamino, hydroxy and alkoxymethyl; or $R_3$ and $R_4$ form a fused 5- to 7-membered saturated ring, optionally containing one or more heteroatoms and optionally substituted by one or more substituents selected from alkyl of 1 to 4 carbon atoms, amino, halo and haloalkyl of 1 to 4 carbon atoms; and DYE is a dye moiety, with the proviso that the dye moiety is not dansyl; or a pharmaceutically acceptable acid addition salt thereof.

The invention additionally provides methods of preparing the dye labeled imidazonaphthyridine, imidazopyridine and imidazoquinoline compounds.

DETAILED DESCRIPTION OF PREFERRED EMBODIMENTS

As mentioned above, the invention provides dye labeled immune response modifying compounds of formula (I):

(I)

wherein:
R₁ is a spacer group;
R₂ is hydrogen, alkyl, hydroxyalkyl, haloalkyl, aminoalkyl, alkylaminoalkyl, dialkylaminoalkyl, amidoalkyl, alkylamidoalkyl, dialkylamidoalkyl, alkanoylalkyl, azidoalkyl, carbamoylalkyl, alkyl optionally interrupted by a heteroatom; alkenyl, alkenyloxyalkyl, cycloalkylalkyl, heterocycloalkyl; aryl, aralkyl, aralkenyl, heteroarylalkyl, in which aryl is optionally substituted by alkyl of 1 to 4 carbon atoms, alkoxy of 1 to 4 carbon atoms, halo, amino, alkylamino or dialkylamino; aroylalkyl, or heteroaroylalkyl;
R₃ and R₄ are each independently hydrogen, alkyl, alkoxy of 1 to 4 carbon atoms, halo, amino, alkylamino, dialkylamino, or when taken together, R₃ and R₄ form a fused aryl or heteroaryl group that is optionally substituted by one or more substituents selected from by alkyl of 1 to 4 carbon atoms, alkoxy of 1 to 4 carbon atoms, halo, amino, alkylamino, dialkylamino, hydroxy and alkoxymethyl; or
R₃ and R₄ form a fused 5- to 7-membered saturated ring, optionally containing one or more heteroatoms and optionally substituted by one or more substituents selected from alkyl of 1 to 4 carbon atoms, amino, halo and haloalkyl of 1 to 4 carbon atoms; and
DYE is dye moiety, with the proviso that the dye moiety is not dansyl; or a pharmaceutically acceptable acid addition salt thereof.

In this document, the following terms have the meanings assigned to them below unless otherwise noted:

Alkyl and alkenyl groups contain from 1 to 8 (or 2 to 8) carbon atoms and may be straight chain or branched. Cycloalkyl groups can contain from 3 to 8 ring members and may be optionally substituted by alkyl groups. Heterocyclic groups can contain from 3 to 8 ring members and from 1 to 3 heteroatoms independently selected from O, S, and N.

Aryl groups are carbocyclic aromatic rings or ring systems. Heteroaryl groups are aromatic rings or ring systems that contain from 1 to 6 heteroatoms independently selected from O, S, and N. A preferred aryl group is benzene. Preferred heteroaryl groups are single rings that have 5 or 6 members and 1 to 4 heteroatoms independently selected from O, S and N.

Heteroatoms are O, S, or N.

The term "oyl" is used to indicate the presence of a carbonyl group in the radical. For example, "aroyl" is used to refer to an aromatic group that is attached by a carbonyl group to the remainder of the structure.

The spacer group is an organic linking group that allows a dye moiety to be attached to an imidazonaphthyridine, imidazopyridine or imidazoquinoline compound without substantially reducing its biological activity. Although the invention is not bound by any theory of operation, it is thought that the spacer group places enough distance between the active core of the molecule and the bulky dye moiety such that the dye moiety does not interfere with the interactions between the active core and the cells that result in cytokine induction. The spacer group can therefore be any divalent organic linking group that does not itself interfere with the biological activity of the molecule and that allows a dye moiety to be included in the molecule without substantially reducing its biological activity. In this context, a compound's biological activity has not been significantly impaired if the labeled compound induces interferon or tumor necrosis factor biosynthesis when tested at a concentration less than or equal to about 50 μg/ml according to Test Method 1 provided below.

One preferred spacer group has the structural formula (II):

(II)

Preferably, when the spacer group has formula (II) the methylene group that is outside the brackets is attached to the dye moiety.

Another preferred spacer group has the structural formula (III):

(III)

The dye moiety can be derived from any of the known dyes, particularly fluorescent dyes, with the proviso that the dye moiety is not dansyl. Examples of suitable types of dyes include dipyrrometheneboron difluoride dyes, fluorescein, fluorescein derivatives, rhodamine, rhodamine derivatives and Texas Red. Many dipyrrometheneboron difluoride (4,4-difluoro-4-bora-3a,4a-diaza-s-indacene) dyes are known, see for example, Haugland, et al, U.S. Pat. No. 4,774,339; Kang, et al. U.S. Pat. No. 5,187,288; Haugland et al., U.S. Pat. No. 5,248,782; and Kang et al., U.S. Pat. No. 5,274,113. Many of the dipyrromethenboron difluoride dyes are commercially available from Molecular Probes, Inc., Eugene, Oregon under the tradename BODIPY® fluorophores. Preferred dye moieties include fluorescein and 4,4-difluoro-5,7-dimethyl-4-bora-3a,4a-diaza-s-indacene which has the following structure.

Preferred compounds of formula (I) include N-[2-(4-amino-2-ethoxymethyl-1H-imidazo[4,5-c]quinolin-1-yl)ethyl]-6-[(4,4-difluoro-5,7-dimethyl-4-bora-3a,4a-diaza-s-indacene-3-propionyl)amino]hexanoamide which has the following structure:

5-{[({4-[4-amino-2-(2-methoxethyl)-1H-imidazo[4,5-c]quinolin-1-yl]butyl}amino)carbonthioyl]amino}-2-(6-hydroxy-3-oxo-3H-xanthen-9-yl)benzoic acid which has the following structure:

and 5-{[({2-[4-amino-2-butyl-1H-imidazo[4,5-c]quinolin-1-yl]ethyl}amino)carbonthioyl]amino}-2-(6-hydroxy-3-oxo-3H-xanthen-9-yl)benzoic acid which has the following structure:

Compounds of the invention may be prepared according to the method shown in Reaction Scheme I below. An imidazonaphthyridine, imidazopyridine or imidazoquinoline of Formula IV is reacted with a dye derivative of Formula V to provide a compound of Formula I. $R_A$ and $R_B$ both contain functional groups which are selected to react with each other. For example, if $R_A$ contains a primary amine, then a dye derivative wherein $R_B$ contains an acyl azide, aldehyde, anhydride, carbonyl halide, halide, haloacetamide, imido ester, isocyanate, isothiocyanate, maleimide, succinimidyl ester or sulfonyl chloride is selected. $R_A$ and $R_B$ are selected such that they react to provide the desired spacer group $R_1$ (e.g., If $R_A$ is —CH$_2$CH$_2$NH$_2$ and $R_B$ is —(CH$_2$)$_2$C(O)NH(CH$_2$)$_5$COOH then $R_1$ will be —CH$_2$CH$_2$NHC(O)(CH$_2$)$_5$NHC(O)(CH$_2$)$_2$—). Methods for preparing compounds of Formula IV where $R_A$ contains a functional group are known. See for example, Gerster, U.S. Pat. No. 4,689,338; Gerster et al., U.S. Pat. No. 4,929,624; Gerster, U.S. Pat. No. 5,268,376; Gerster et al., U.S. Pat. No. 5,389,640; Nikolaides et al., U.S. Pat. No. 5,352,784; Lindstrom et al., U.S. Pat. No. 5,494,916; Andre, et. al, U.S. Pat. No. 4,988,815; Gerster, U.S. Pat. No. 5,367,076; Gerster, U.S. Pat. No. 5,175,296; Nikolaides et. al., U.S. Pat. No. 5,395,937; Gerster et. al., U.S. Pat. No. 5,741,908; Lindstrom, U.S. Pat. No. 5,693,811; Nanba et al., U.S. Pat. No. 6,069,149, the disclosures of which are incorporated by reference herein. See also, International Publication WO 99/29693. Many dye derivatives containing a reactive functional group are commercially available (e.g. BODIPY® fluorophores, fluorescein isothiocyanate, 5-carboxyfluorescein) or may be prepared by known synthetic routes. See for example, Haugland, et al, U.S. Pat. No. 4,774,339; Kang, et al. U.S. Pat. No. 5,187,288; Haugland et al., U.S. Pat. No. 5,248,782; and Kang et al., U.S. Pat. No. 5,274,113, the disclosures of which are incorporated by reference herein. The reaction will generally be conducted by combining a solution of the compound of Formula IV in a suitable solvent such as pyridine or dimethyl sulfoxide with a solution of the dye derivative of Formula V in a suitable solvent such as pyridine or dimethylsulfoxide. The reaction may be run at ambient temperature or at an elevated temperature. The product of Formula I is then isolated and purified using conventional methods.

Reaction Scheme I

The examples below are provided to illustrate the invention, but are not intended to limit it in any way.

CYTOKINE INDUCTION IN HUMAN CELLS—
TEST METHOD 1

An in vitro human blood cell system is used to assess cytokine induction by compounds of the invention. Activity is based on the measurement of interferon and tumor necrosis factor ($\alpha$) (IFN and TNF, respectively) secreted into culture media as described by Testerman et. al. in "Cytokine Induction by the Immunomodulators Imiquimod and S27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMCs) are separated from whole blood by Histopaque®-1077 (Sigma Chemicals, St. Louis, Mo.) density gradient centrifugation. The PBMCs are washed twice with Hank's Balanced Salts Solution (Sigma) and are then suspended at $2 \times 10^6$ cells/mL in RPMI 1640 medium containing 10% fetal bovine serum, 2 mM L-glutamine and 1% penicillin/streptomycin solution (RPMI complete). 1 mL portions of PBMC suspension are added to 12 or 24 well flat bottom sterile tissue culture plates.

Compound Preparation

The compounds are solubilized in ethanol, dimethyl sulfoxide or pyrogen free water then diluted with tissue culture water, 0.01N sodium hydroxide or 0.01N hydrochloric acid (The choice of solvent will depend on the chemical characteristics of the compound being tested.). Ethanol or DMSO concentration should not exceed a final concentration of 1% for addition to the culture wells. The compounds are generally tested using a concentration range from about 0.01 µg/mL to about 50 µg/mL.

Incubation

The solution of test compound is added to the wells containing 1 ml of PBMCs in media. The plates are covered with plastic lids, mixed gently and then incubated for 24 hours at 37° C. with a 5% carbon dioxide atmosphere.

Separation

Following incubation the cell-free culture supernatant is removed with a sterile polypropylene pipet and transferred to a 12×75 mm polypropylene tube. The tubes are then centrifuged at 1000 rpm (~800×g) for 10 to 15 minutes at 4° C. The supernatant is removed and placed into 2 mL sterile freezing vials. Samples are maintained at −70° C. until analyzed for cytokines.

Interferon Analysis/Calculation

Interferon concentrations are determined by bioassay using A549 human lung carcinoma cells challenged with encephalomyocarditis. The details of the bioassay method have been described by G. L. Brennan and L. H. Kronenberg in "Automated Bioassay of Interferons in Micro-test Plates", Biotechniques, June/July, 78, 1983, incorporated herein by reference. Briefly stated the method is as follows: A549 cells are incubated with dilutions of IFN standard or test samples at 37° C. for 24 hours. The incubated cells are then infected with an inoculum of encephalomyocarditis virus. The infected cells are incubated for an additional 24 hours at 37° C. before quantifying for viral cytopathic effect. The viral cytopathic effect is quantified by staining of the wells with a vital dye such as crystal violet followed by visual scoring of the plates. Results are expressed as alpha reference units/mL based on the value obtained for an NIH Human Leukocyte IFN standard.

Tumor Necrosis Factor ($\alpha$) Analysis

Tumor necrosis factor ($\alpha$) (TNF) concentration is determined using an ELISA kit available from Genzyme, Cambridge, Mass. The results are expressed as pg/ml.

CYTOKINE INDUCTION IN HUMAN CELLS—
TEST METHOD 2

An in vitro human blood cell system is used to assess cytokine induction. Activity is based on the measurement of interferon and tumor necrosis factor ($\alpha$) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMCs) are separated from whole blood by density gradient centrifugation using Histopaque®-1077. The PBMCs are washed twice with Hank's Balanced Salts Solution and then are suspended at $3-4 \times 10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 0.12 to 30 µM.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (0.12 to 30 µM). The final concentration of PBMC suspension is 1.5–2× $10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) and for tumor necrosis factor (α) by ELISA Interferon (α) and Tumor Necrosis Factor (α) Analysis by ELISA Interferon (α) concentration is determined by ELISA using a Human Multi-Species kit from PBL Biomedical Laboratories, New Brunswick, N.J. Results are expressed in pg/mL.

Tumor necrosis factor (α) (TNF)concentration is determined using ELISA kits available from Genzyme, Cambridge, Mass; R&D Systems, Minneapolis, Minn.; or Pharmingen, San Diego, Calif. Results are expressed in pg/mL.

Preparation of an Unlabeled Compound of Formula IV 2-(4-Amino-2-ethoxymethyl-1H-imidazo[4,5-c] quinolin-1-yl)ethaneamine trihydrochloride Part A Thionyl chloride (32.3 mL, 0.4338 mole) and N,N-dimethylformamide (32 mL, 0.4338 mole) were added sequentially to a suspension of 4-hydroxy-3-nitroquinoline (75 g, 0.3944 mole) in dichloromethane (750 ml). The reaction mixture was heated at reflux for about 2½ hours and then held at ambient temperature overnight. The reaction mixture was chilled in an ice bath and then a mixture of triethylamine (82.5 mL, 0.5916 moles) and ethanolamine (35.7 mL, 0.5916 mole) in dichloromethane was slowly added. The reaction mixture was heated at reflux for several hours and then an additional 0.5 equivalents of both triethylamine and ethanolamine were added. The reaction mixture was refluxed for an additional hour then held at ambient temperature overnight. The resulting solid was isolated by filtration, washed first with dichloromethane then with water, and dried to provide 75 g of 2-[(3-nitro-4-quinolinyl) amino]ethanol.

Part B

2-[(3-Nitro-4-quinolinyl)amino]ethanol (6 g) was combined with ethanol (200 mL) and platinum on carbon catalyst. The mixture was hydrogenated on a Parr apparatus. This procedure was repeated four additional times using a total of 30 g of starting material. The mixtures from all five hydrogenations were combined and then filtered through a layer of Celite® filter aid to remove the catalyst. The filtrate was concentrated under vacuum to provide crude 2-[(3-amino-4-quinolinyl)amino]ethanol.

Part C

The crude material from Part B was combined with ethoxyacetic acid (13.4 g). The mixture was heated using an oil bath until the reaction was complete. The mixture was cooled to ambient temperature and then diluted with water and made basic with sodium hydroxide (6N). The mixture was extracted 3 times with dichloromethane. The extracts were combined, washed with water, dried with magnesium sulfate and then filtered. The filtrate was concentrated under vacuum to provide 30.8 g of crude 2-ethoxymethyl-1H-imidazo[4,5-c]quinoline-1-ethanol.

Part D

Peracetic acid (25 mL of 32%) was added to a mixture of the material from Part C and methyl acetate (350 mL). The reaction mixture was heated at 54° C. until thin layer chromatography indicated that all of the starting material had been consumed. The reaction mixture was cooled to ambient temperature. A solid was isolated by filtration, washed with methyl acetate and then dried to provide 28.5 g of 2-ethoxymethyl-1-(2-hydroxyethyl)-1H-imidazo[4,5-c] quinoline 5N oxide (crop 1). The filtrate was concentrated under vacuum. The residue was diluted with aqueous sodium bicarbonate and then extracted 3 times with dichloromethane. The extracts were combined, washed once with aqueous sodium bicarbonate, washed twice with water, dried with magnesium sulfate, filtered and then concentrated under vacuum to provide 1.6 g of additional product (crop 2).

Part E

Crops 1 and 2 from Part D were combined and mixed with dichloromethane (600 mL). Concentrated ammonium hydroxide (450 mL) was added. The reaction mixture was cooled in an ice bath and then p-toluenesulfonyl chloride (22 g) was slowly added to the mixture. The reaction mixture was stirred at ambient temperature overnight. Thin layer chromatography indicated the presence of a trace of starting material so 1 g of p-toluenesulfonyl chloride was added and the reaction mixture was stirred for an additional hour. A solid was isolated by filtration, washed with dichloromethane and then dried to provide 20.2 g of crude 4-amino-2-ethoxymethyl-1H-imidazo[4,5-c]quinoline-1-ethanol. A 1 g portion of this material was dissolved in acetone (about 10 mL). Hydrogen chloride/methanol (1 g/5 mL) was added until the solution became acidic. A precipitate formed immediately. The mixture was heated on a steam bath for 10 minutes. The solid was isolated by filtration, washed with acetone and then recrystallized from methanol/ acetone to provide 0.7 g of 4-amino-2-ethoxymethyl-1H-imidazo[4,5-c]quinoline-1-ethanol hydrochloride as an off-white solid. Analysis: Calculated for $C_{15}H_{19}ClN_4O$: % C, 55.81; % H, 5.93; % N, 17.36; Found: % C, 55.91; % H, 5.90; % N, 17.35.

Part F

Thionyl chloride (5 mL) and 4-amino-2-ethoxymethyl-1H-imidazo[4,5-c]quinoline-1-ethanol (1 g) were combined and heated on a steam bath until thin layer chromatography (20% methanol/ethyl acetate) showed the disappearance of starting material. The reaction mixture was cooled to ambient temperature and then slowly poured into a mixture of ice and water. The mixture was neutralized with sodium bicarbonate and then extracted 3 times with dichloromethane. The extracts were combined, washed 3 times with aqueous sodium bicarbonate, dried with magnesium sulfate, filtered and then concentrated under vacuum. Acetone (about 10 mL) was added to the residue followed by methanolic hydrogen chloride (about 1 mL). The mixture was refluxed and a precipitate formed. The reaction mixture was cooled to ambient temperature. The precipitate was isolated by filtration and then washed with acetone. The solid was dissolved in hot methanol and then precipitated by the addition of acetone. The precipitate was isolated by filtration, washed with water and then dried to provide 1-(2-chloroethyl)-2-ethoxymethyl-1H-imidazo[4,5-c]quinolin-4-amine hydrochloride. Analysis: Calculated for $C_{15}H_{18}ClN_4$: % C, 52.80; % H, 5.32; % N, 16.42; Found: % C, 52.67; % H, 5.21; % N, 16.29.

Part G

Sodium azide (14.7 g) was added to a solution of 1-(2-chloroethyl)-2-ethoxymethyl-1H-imidazo[4,5-c]quinolin-4-amine (22.8 g prepared according to the method of Part F) in N,N-dimethylformamide (75 mL). The reaction mixture was heated at reflux for several hours and then allowed to cool to ambient temperature overnight. The reaction mixture was poured into water (100 ml) and then extracted 3 times with ethyl acetate. The extracts were combined, washed 3 times with water, dried over magnesium sulfate, filtered and then concentrated to dryness under vacuum to provide crude 1-(2-azidoethyl)-2-ethoxymethyl-1H-imidazo[4,5-c]quinolin-4-amine as an oil.

Part H

Platinum on carbon catalyst was added to a solution of the crude material from Part G in ethanol (250 mL). The mixture was reduced on a Parr apparatus. The bottle was evacuated several times to remove nitrogen and the progress of the reaction was monitored by thin layer chromatography. The reaction mixture was filtered through a layer of Celite® filter aid to remove the catalyst and the filter pad was washed with warm ethanol. The filtrate was concentrated under vacuum to provide an oil which was purified by column chromatography (silica gel eluting with methanol/ethyl acetate). An attempt to recrystallize the purified oil produced a precipitate which was isolated by filtration. The filtrate was concentrated under vacuum to provide an oil. The oil was dissolved in ethanol. A portion was removed for later use. The remainder was combined with 10% hydrogen chloride in ethanol and refluxed. The mixture was cooled in an ice bath and then filtered to isolate the resulting solid. The solid was recrystallized from ethanol to provide 2-(4-amino-2-ethoxymethyl-1H-imidazo[4,5-c]quinolin-1-yl)ethaneamine trihydrochloride. Analysis: Calculated for $C_{15}H_{22}Cl_3N_5O$: % C, 45.64; % H, 5.62; % N, 17.74; Found: % C, 46.14; % H, 5.64; % N, 17.83.

EXAMPLE 1

Preparation of a Labeled Compound of Formula I

N-[2-(4-Amino-2-ethoxymethyl-1H-imidazo[4,5-c]quinolin-1-yl)ethyl]-6-[(4,4-difluoro-5,7-dimethyl-4-bora-3a,4a-diaza-s-indacene-3-propionyl)amino]hexanoamide A solution containing 6-((4,4-difluoro-5,7-dimethyl-4-bora-3a,4a-diaza-s-indacene-3-propionyl)amino)hexanoic acid, succinimidyl ester (5 mg, BODIPY® FL-X,SE from Molecular Probes) dissolved in dimethyl sulfoxide (1 mL) was combined with 2-(4-amino-2-ethoxymethyl-1H-imidazo[4,5-c]quinolin-1-yl)ethaneamine trihydrochloride (2.5 mg). Pyridine (5 drops) was added and the reaction mixture was shaken overnight at ambient temperature. The reaction mixture was purified by high performance liquid chromatography using a Bondapak C18 12.5 nm reverse phase column (available from Waters, Milford, Mass.) eluting with a composite gradient of acetonitrile in water. In a typical elution, the acetonitrile content was increased from 5% to 30% during the initial 15 minutes, followed by a 10 minute isocratic elution at 30% acetonitrile, a 5 minute gradient to 50% acetonitrile, then a 5 minute isocratic elution at 50% acetonitrile. All solvents contained 0.1% trifluoroacetic acid. The fractions containing the labeled compound were initially identified by comparing chromatograms of the free fluorophore and the unlabeled compound with that of the reaction mixture. The fractions containing the labeled compound were then collected, pooled and lyophilized. The labeled compound had a molecular mass of 672.08 as determined by electrospray mass spectroscopy. The calculated mass is 672.35 based on the proposed empirical formula $C_{35}H_{45}N_8O_3BF_2$. The uv-visible absorption spectra showed absorption bands at 505 nm and 325 nm which are characteristic of the fluorescent label and of the unlabeled compound respectively.

The labeled compound of Example 1 and the unlabeled intermediate (2-(4-amino-2-ethoxymethyl-1H-imidazo[4,5-c]quinolin-1-yl)ethaneamine trihydrochloride) were tested side by side for their ability to induce cytokine biosynthesis using Test Method 1 described above. The compound of Example 1 was solubilized in ethanol. The unlabeled intermediate was solubilized in tissue culture water. The results are shown in the table below.

| | Cytokine Induction | | | |
|---|---|---|---|---|
| Concentration | Labeled Compound of Example 1 | | Unlabeled Intermediate | |
| (µg/ml) | TNF (pg/ml) | IFN (U/ml) | TNF (pg/ml) | IFN (U/ml) |
| 10 | Not run | Not run | 2640 | 140 |
| 3 | 869 | 62 | 538 | 81 |
| 1 | 369 | 421 | 49 | 2878 |
| 0.3 | 73 | 2878 | 0 | 2878 |
| 0.1 | 46 | 554 | 0 | 421 |
| 0.03 | 42 | 47 | Not run | Not run |
| 0.01 | 0 | 16 | Not run | Not run |

Flow Cytometry Analysis

Whole blood was collected by venipuncture into EDTA vacutainer tubes from healthy human donors. PBMCs were separated from whole blood by ficoll hypaque (Sigma Chemicals, St. Louis, Mo.) density gradient centrifugation as described in Testerman. The PBMCs were suspended at $2 \times 10^6$ cells/mL in RPMI 1640 medium containing 10% fetal bovine serum, 2 mM L-glutamine and penicillin/streptomycin solution (RPMI complete). The cells were then incubated in 12×75 mm polypropylene tubes for 1 hour at 37° C. with either the labeled compound of Example 1 or with the BODIPY fluorophore used to prepare the labeled compound. Following incubation the cells were washed two times with staining buffer (Dulbecco's Phosphate Buffered Saline without calcium and magnesium, 1% heat inactivated fetal bovine serum, and 0.1% sodium azide). The cells were suspended in staining buffer and transferred to 12×75 mm polystyrene tubes for analysis by flow cytometry. Binding to mononuclear cells was determined by fluorescence using a FACScan flow cytometer (purchased from Becton Dickinson).

Figure 1:
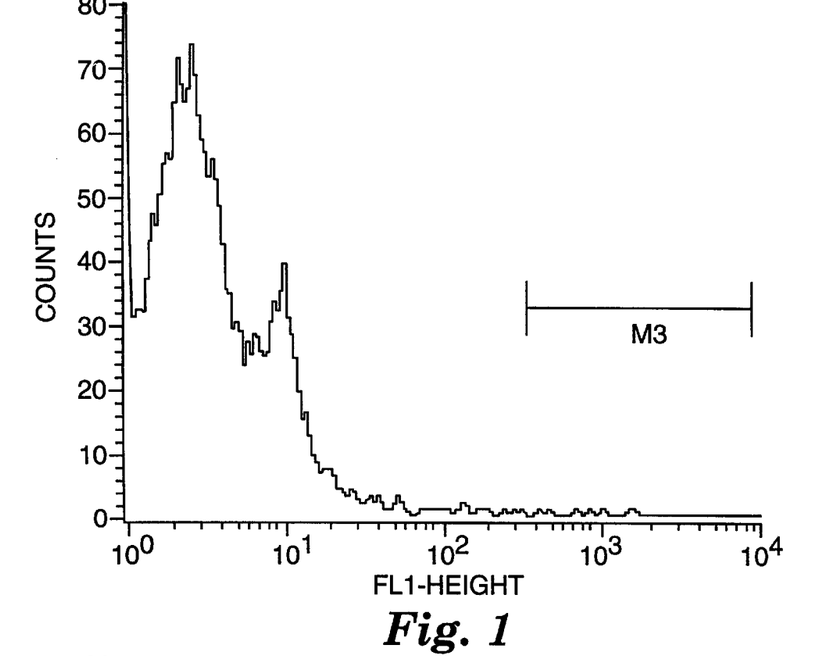
FIG. 1 is a histogram plot of the fluorescence intensity from cells incubated with fluorescent dye alone.
Figure 2:
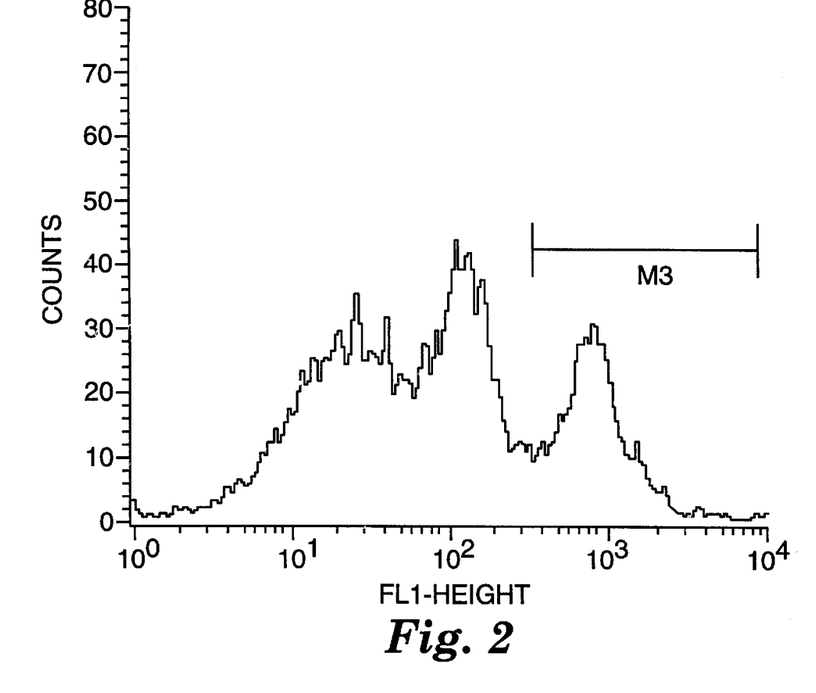
FIG. 2 is a histogram plot of the fluorescence intensity from cells incubated with a labeled compound of the invention where the label is the dye used in the incubation of FIG. 1.

The histograms of FIGS. 1 and 2 plot the fluorescence intensity with the more highly fluorescent cell populations being seen further to the right. The peak area labeled as M3 in the histograms indicates the fluorescence binding to the monocyte population in the peripheral blood mononuclear cells. These monocytes have been shown to be a major cell producing cytokines in response to the imidazoquinolines (Gibson et. al. In "Cellular Requirements for Cytokine Production in Response to the Immunomodulators Imiquimod and S-27609", Journal of Interferon and Cytokine Research, 15, 537–545 (1995). The histogram of FIG. 1 was obtained from cells incubated with the BODIPY fluorophore. The histogram of FIG. 2 was obtained from cells incubated with the BODIPY labeled compound of Example 1. These histograms demonstrate that the labeled compound of Example 1 binds to human peripheral blood mononuclear cells whereas the BODIPY fluorophore by itself does not and that monocytes bind more effectively than other PBMCs.

The labeled compound of Example 1 did not show significant binding to monocytes when incubated with human PBMCs at 4° C. for 1 hour. A histogram similar to that of FIG. 1 was obtained indicating that binding is likely intracellular.

Preparation of an Unlabeled Compound of Formula IV 4-(4-Amino-2-(2-methoxyethyl)-1H-imidazo[4,5-c]quinolin-1-yl)butaneamine Part A Phosphorous oxychloride (30 mL, 0.32 mole) was slowly added over a period of 1 hour to a solution of 3-nitroquinolin-4-ol (50 g, 0.26 mole) in N,N-dimethylformamide (150 mL). The reaction mixture was heated on a steam bath for half an hour and then poured over a mixture of ice and water. The resulting solid was isolated by filtration and then suspended in chloroform (750 mL). The suspension was heated on a steam bath and then filtered while still hot. The filtrate was poured into a separatory funnel and the chloroform layer was separated from the residual water. Triethylamine (29 mL) was added to the chloroform layer followed by the slow addition of tert-butyl N-(4-aminobutyl)carbamate. The reaction was monitored by thin layer chromatography. When all of the starting material was gone, the reaction mixture was washed with water, dried over magnesium sulfate and then concentrated under vacuum to provide 66 g of 1,1-dimethylethyl N-{4-[(3-nitroquinolin-4-yl)amino]butyl}carbamate as a yellow solid.

Part B

Platinum on carbon (3.6 g of 5%) was added to a solution of 1,1-dimethylethyl N-{4-[(3-nitroquinolin-4-yl)amino]butyl}carbamate (36.1 g, 100 mmol) in toluene (1.5 L). The mixture was hydrogenated at 50 psi (3.5 Kg/cm$^2$) for 3 hours. The reaction mixture was filtered through a layer of Celite® filter aid to remove the catalyst. The filtrate was concentrated under vacuum to provide 30.1 g of crude 1,1-dimethylethyl N-{4-[(3-aminoquinolin-4-yl)amino]butyl}carbamate as a gooey orange syrup.

Part C

Under a nitrogen atmosphere, a solution of the material from Part B in dichloromethane (1 L) was cooled to 0° C. Triethylamine (13 mL, 93.3 mmol)) was added. Methoxypropionyl chloride (11.5 g, 91.2 mmol) was added over a period of 10 minutes. The ice bath was removed. After 1 hour the reaction mixture was concentrated to provide a pale orange solid. This material was combined with ethanol (1 L) and triethylamine (39 mL). The mixture was heated at about 75° C. overnight. The reaction mixture was allowed to cool to ambient temperature and then it was concentrated under vacuum to provide an oil. The oil was combined with diethyl ether (750 mL), stirred for about 15 minutes and then filtered. The filtrate was concentrated under vacuum to provide 34.5 g of crude 1,1-dimethylethyl N-[4-(2-(2-methoxyethyl)-1H-imidazo[4,5-c]quinolin-1-yl)butyl]carbamate as a brown syrup.

Part D

Under a nitrogen atmosphere, 3-chloroperbenzoic acid (12.86 g of >77%) was added to a solution of 1,1-dimethylethyl N-[4-(2-(2-methoxyethyl)-1H-imidazo[4,5-c]quinolin-1-yl)butyl]carbamate (21.3 g, 53.5 mmol) in dichloromethane (200 mL). The reaction mixture was allowed to stir at ambient temperature overnight. Additional 3-chloroperbenzoic acid (200 mg of >77%) was added. After about 2 hours the reaction mixture was washed with water, aqueous sodium bicarbonate, water and finally with brine. The organic layer was dried over sodium sulfate and then concentrated under nitrogen to provide 22 g of crude 1-{4-[(1,1-dimethylethylcarbonyl)amino]butyl}-2-(2-methoxyethyl)-1H-imidazo[4,5-c]quinoline-5N-oxide as a sticky syrup.

Part E

Concentrated ammonium hydroxide (~50 mL) was added to a solution of the material from Part D in dichloromethane (200 mL). Under a nitrogen atmosphere, the reaction mixture was cooled to 0° C. Tosyl chloride (10.2 g, 53.5 mmol) was added with rapid stirring over a period of 10 minutes. The ice bath was removed and the reaction mixture was allowed to stir at ambient temperature. The layers were separated. The organic layer was washed with 1% sodium carbonate (3×), water and brine; dried over sodium sulfate and then concentrated under vacuum to provide 20.0 g of crude 1,1-dimethylethyl N-[4-(4-amino-2-(2-methoxyethyl)-1H-imidazo[4,5-c]quinolin-1-yl)butyl]carbamate as a mustard yellow solid.

Part F

A mixture of 1,1-dimethylethyl N-[4-(4-amino-2-(2-methoxyethyl)-1H-imidazo[4,5-c]quinolin-1-yl)butyl]carbamate (18.0 g) and hydrogen chloride/ethanol (40 mL of 2M) was heated to about 70° C. After 90 minutes another 40 mL of hydrogen chloride/ethanol was added. After about an additional hour, the reaction mixture was allowed to cool while being purged with nitrogen to remove excess hydrogen chloride. The reaction mixture was concentrated to near dryness. The residue was triturated with diethyl ether. The resulting solid was isolated by filtration and then dried under high vacuum to provide 15.8 g of the dihydrochloride salt as a light brown solid.

A portion of the salt (10 g) was dissolved in water. The solution was adjusted to pH 11 by the addition of ammonium hydroxide and then it was extracted several times with chloroform. The extracts were combined and concentrated under vacuum. The residue was slurried with toluene and then concentrated to dryness (3×) to provide 6.6 g of 4-(4-amino-2-(2-methoxyethyl)-1H-imidazo[4,5-c]quinolin- 1-yl)butaneamine as a brown/yellow solid.

EXAMPLE 2

Preparation of a Labeled Compound of Formula I

5-{[({4-[4-Amino-2-(2-methoxyethyl)-1H-imidazo[4,5-c]quinolin-1-yl]butyl}amino)carbonthioyl]amino}-2-(6-hydroxy-3-oxo-3H-xanthen-9-yl)benzoic Acid A solution of 4-(4-amino-2-(2-methoxyethyl)-1H-imidazo[4,5-c]quinolin-1-yl)butaneamine (0.11 g, 0.35 mmol) in warm pyridine (2 mL) was slowly added to a solution of fluorescein-5-isothiocyanate (0.138 g, 0.35 mmol) in warm pyridine (2 mL). The reaction mixture was maintained at ambient temperature overnight. The reaction mixture was quenched with methanol (15 mL) and then stirred for an hour. The resulting solid was isolated by filtration, slurried with boiling methanol, and then dried to provide 0.12 g of the desired product as an orange solid, m.p. >245°. Analysis by both thin layer chromatography and high performance liquid chromatography indicated pure product. Analysis: Calculated for $C_{38}H_{34}N_6O_6S$: % C, 64.94; % H, 4.88; % N, 11.96; Found: % C, 61.33; % H, 5.09; % N, 11.39. High resolution mass spectroscopy: TM=703.2339 Da., MM=703.2315 Da.

Preparation of an Unlabeled Compound of Formula IV 2-(4-Amino-2-butyl-1H-imidazo[4,5-c]quinolin-1-yl)ethaneamine Part A Triethylamine (66.8 g, 0.66 mmol) was added to a solution of tert-butyl (N-2-aminoethyl)carbamate (55.0 g, 0.34 mmol) in anhydrous dichloromethane (500 mL). 4-Chloro-3-nitroquinoline (68.2 g, 0.33 mmol) was slowly added. The reaction mixture exothermed. The reaction mixture was allowed to stir overnight. The resulting precipitate was isolated by filtration and rinsed with water to provide a yellow solid. The filtrate was washed with water, dried over magnesium sulfate and then concentrated to provide a yellow solid. The two batches of solid were combined, slurried with hexane, filtered and then dried to provide 101 g of 1,1-dimethylethyl N-{2-[(3-nitroquinolin-4-yl)amino]ethyl}carbamate as a yellow solid.

Part B

Platinum on carbon (1.0 g of 10%) and sodium sulfate (2 g) were added to a slurry of 1,1-dimethylethyl N-{2-[(3-nitroquinolin-4-yl)amino]ethyl}carbamate (100 g, 0.30 mol) in toluene (500 mL). The reaction vessel was placed on a Parr apparatus under 50 psi (3.5 Kg/cm$^2$) hydrogen pressure overnight at ambient temperature. The reaction mixture was filtered through a layer of Celite® filter aid to remove the catalyst. The filtrate was concentrated under vacuum to provide 73 g of 1,1-dimethylethyl N-{2-[(3-aminoquinolin-4-yl)amino]ethyl}carbamate as a dark gold oil. Thin layer chromatography (silica gel; 10% methanol in dichloromethane) analysis indicated that the material was pure.

Part C

Trimethylorthovalerate (5.9 g, 36.4 mmol) was added with stirring to a solution of 1,1-dimethylethyl N-{2-[(3-aminoquinolin-4-yl)amino]ethyl}carbamate (10.0 g, 33.1 mmol) in anhydrous toluene (100 mL). The reaction mixture was heated to reflux. A 10 mL portion of toluene was removed using a Dean Stark trap and the reaction mixture was maintained for 36 hours. An additional 40 mL of toluene was removed and then the reaction was allowed to cool to ambient temperature with continued stirring. The resulting precipitate was isolated by filtration and dried to provide 6.2 g of 1,1-dimethylethyl N-[2-(2-butyl-1H-imidazo[4,5-c]quinolin-1-yl)ethyl]carbamate as a tan solid. Thin layer chromatography (silica gel; 10% methanol in dichloromethane) analysis indicated that the material was pure.

Part D

3-Chloroperbenzoic acid (5.15 g of 60%, 17.9 mmol) was slowly added with vigorous stirring to a solution of 1,1-dimethylethyl N-[2-(2-butyl-1H-imidazo[4,5-c]quinolin-1-yl)ethyl]carbamate (6.0 g, 16.3 mmol) in chloroform (60 mL). The reaction mixture was maintained at ambient temperature overnight and then it was quenched with aqueous sodium carbonate (250 mL of 1%). The layers were separated. The organic layer was dried over magnesium sulfate and then concentrated under vacuum to provide ~6.3 g of 1-{2-[(1,1-dimethylethylcarbonyl)amino]ethyl}-2-butyl-1H-imidazo[4,5-c]quinoline-5N-oxide as a tan foam.

Part E

A solution of 1-{2-[(1,1-dimethylethylcarbonyl)amino]ethyl}-2-butyl- 1H-imidazo[4,5c]quinoline-5N-oxide (39 g, 101 mmol) in chloroform (300 mL) was cooled in an ice bath. Trichloroacetyl isocyanate (21 g, 112 mmol) was added with stirring. The reaction mixture was maintained at ambient temperature overnight. The reaction mixture was quenched with concentrated ammonium hydroxide (40 mL) and then stirred at ambient temperature for 4 hours. Water was added to the reaction mixture. The layers were separated. The organic layer was dried over magnesium sulfate and then concentrated under vacuum to provide a gold oil. This material was recrystallized from 90% isopropanol to prove 30.2 g of 1,1-dimethylethyl N-[2-(4-amino-2-butyl-1H-imidazo[4,5-c]quinolin-1-yl)ethyl]carbamate.

Part F

Trifluoroacetic acid (100 mL) was added with stirring to a solution of 1,1-dimethylethyl N-[2-(4-amino-2-butyl-1H-imidazo[4,5-c]quinolin-1-yl)ethyl]carbamate (30.0 g, 78.2 mmol) in acetonitrile (100 mL). The reaction mixture was maintained at ambient temperature for 24 hours and then it was concentrated under vacuum. The residue was dissolved in a minimal amount of water and the pH of the solution was adjusted to pH 13 using 10% sodium hydroxide. The resulting precipitate was isolated by filtration and dried under high vacuum to provide 18.1 g of 2-(4-amino-2-butyl-1H-imidazo[4,5-c]quinolin-1-yl)ethaneamine as an off-white solid, m.p. 196–199° C.

EXAMPLE 3

Preparation of a Labeled Compound of Formula I

5-{[({2-[4-Amino-2-butyl-1H-imidazo[4,5-c]quinolin-1-yl]ethyl}amino)carbonthioyl]amino}-2-(6-hydroxy-3-oxo-3H-xanthen-9-yl)benzoic Acid

A solution of fluorescein-5-isothiocyanate (778 mg, 2.0 mmol) in pyridine (5 mL) was added to a solution of 2-(4-amino-2-butyl-1H-imidazo[4,5-c]quinolin-1-yl)ethaneamine (566 mg, 2.0 mmol) in pyridine (5 mL). The reaction mixture was heated at reflux for 30 minutes and then poured into water (50 mL). The resulting orange solid was isolated by filtration, dried under high vacuum and then recrystallized from pyridine to provide 0.76 g of the desired product as an orange solid, m.p. >245°. Analysis by high performance liquid chromatography indicated pure product. Analysis: Calculated for $C_{37}H_{32}N_6O_5S$: % C, 66.06; % H, 4.79; % N, 12.49; Found: % C, 63.03; % H, 4.89; % N, 12.59. High resolution mass spectroscopy: TM=673.2233 Da., MM=673.2251 Da.

The labeled compounds of Examples 2 and 3 were tested for their ability to induce cytokine biosynthesis using Test Method 2 described above. The results are shown in the table below where a "+" indicates that the compound induced the indicated cytokine at that particular concentration and a "−" indicates that the compound did not induce the indicated cytokine at that particular concentration.

| Concentration | Cytokine Induction | | | |
|---|---|---|---|---|
| | Example 2 | | Example 3 | |
| (μg/ml) | TNF | IFN | TNF | IFN |
| 30 | + | + | + | + |
| 10 | + | + | − | + |
| 3.33 | + | − | − | − |
| 1.11 | − | − | − | − |
| 0.37 | − | − | − | − |
| 0.12 | − | − | − | − |
| 0.041 | − | − | − | − |
| 0.014 | − | − | − | − |

What is claimed is:

1. A compound of the formula (I):

wherein:

$R_1$ is a spacer group selected from the group consisting of

$R_2$ is hydrogen, alkyl, hydroxyalkyl, haloalkyl, aminoalkyl, alkylaminoalkyl, dialkylaminoalkyl, amidoalkyl, alkylamidoalkyl, dialkylamidoalkyl, alkanoylalkyl, azidoalkyl, carbamoylalkyl, alkyl optionally interrupted by a heteroatom; alkenyl, alkenyloxyalkyl; cycloalkylalkyl, heterocycloalkyl; aryl, aralkyl, aralkenyl, heteroarylalkyl, in which aryl is optionally substituted by alkyl of 1 to 4 carbon atoms, alkoxy of 1 to 4 carbon atoms, halo, amino, alkylamino or dialkylamino; aroylalkyl, or heteroaroylalkyl;

$R_3$ and $R_4$ are each independently hydrogen, alkyl, alkoxy of 1 to 4 carbon atoms, halo, amino, alkylamino, or dialkylamino, or when taken together, $R_3$ and $R_4$ form a fused aryl group that is optionally substituted by one or more substituents selected from alkyl of 1 to 4 carbon atoms, alkoxy of 1 to 4 carbon atoms, halo, amino, alkylamino, dialkylamino, hydroxy and alkoxymethyl; and DYE is a dye moiety selected from the group consisting of dipyrromethenebor on difluoride dyes, fluorescein dyes, rhodamine dyes and Texas Red, or a pharmaceutically acceptable acid addition salt thereof.

2. The compound of claim 1 wherein the fluorescent dye moiety is a dipyrromethenebor on difluoride dye.

3. The compound of claim 1 wherein DYE has the following structure:

4. The compound of claim 1 wherein the fluorescent dye moiety is fluorescein.

5. The compound of claim 1 wherein $R_3$ and $R_4$ together form a fused aryl group, optionally containing one or more heteroatoms and optionally substituted by one or more substituents selected from alkyl of 1 to 4 carbon atoms, alkoxy of 1 to 4 carbon atoms, halo, amino, alkylamino, dialkylamino, hydroxy and alkoxymethyl.

6. The compound of claim 1 wherein $R_3$ and $R_4$ together form a benzene ring.

7. The compound of claim 1 wherein $R_3$ and $R_4$ are each independently hydrogen, a straight or branched alkyl of 1 to 8 carbon atoms, alkoxy of 1 to 4 carbon atoms, halo, amino, alkylamino or dialkylamino.

8. The compound of claim 1 wherein $R_2$ is hydrogen, alkyl containing 1 to 8 carbon atoms, or alkoxyalkyl wherein the alkoxy group contains 1 to 4 carbon atoms and the alkyl group contains 1 to 4 carbon atoms.

9. The compound of claim 1 having the following structure:

10. The compound of claim 1 having the following structure

11. The compound of claim 1 having the following structure

* * * * *